(12) United States Patent
Ambrose et al.

(10) Patent No.: US 9,326,059 B2
(45) Date of Patent: Apr. 26, 2016

(54) INFLATABLE BUBBLE

(71) Applicant: Asius Technologies, LLC, Longmont, CO (US)

(72) Inventors: Stephen D. Ambrose, Longmont, CO (US); Samuel P. Gido, Hadley, MA (US); Robert B. Schulein, Schaumburg, IL (US)

(73) Assignee: ASIUS TECHNOLOGIES, LLC, Longmont, CO (US)

( * ) Notice: Subject to any disclaimer, the term of this patent is extended or adjusted under 35 U.S.C. 154(b) by 0 days.

(21) Appl. No.: 14/524,627

(22) Filed: Oct. 27, 2014

(65) Prior Publication Data

US 2015/0163586 A1    Jun. 11, 2015

Related U.S. Application Data

(63) Continuation of application No. 13/086,138, filed on Apr. 13, 2011, now abandoned, which is a continuation-in-part of application No. 12/777,001, filed on May 10, 2010, now Pat. No. 8,391,534, and a continuation-in-part of application No. 12/178,236, filed on Jul. 23, 2008, now Pat. No. 8,340,310.

(60) Provisional application No. 61/323,599, filed on Apr. 13, 2010.

(51) Int. Cl.
| | |
|---|---|
| *H04R 1/10* | (2006.01) |
| *H04R 25/00* | (2006.01) |
| *H04R 1/20* | (2006.01) |
| *H04R 1/32* | (2006.01) |
| *A61F 11/00* | (2006.01) |

(52) U.S. Cl.
CPC .............. *H04R 1/323* (2013.01); *A61F 11/006* (2013.01); *H04R 1/1016* (2013.01); *H04R 1/1091* (2013.01)

(58) Field of Classification Search
CPC .......................................................... H04R 1/10
USPC ................... 381/74, 328, 338, 380, 322, 71.6
See application file for complete search history.

(56) References Cited

U.S. PATENT DOCUMENTS

| | | | | |
|---|---|---|---|---|
| 6,094,494 | A * | 7/2000 | Haroldson ..................... | 381/328 |
| 8,213,629 | B2 * | 7/2012 | Goldstein et al. ............... | 381/74 |
| 8,473,081 | B2 * | 6/2013 | Usher et al. ..................... | 700/94 |
| 2009/0290721 | A1 * | 11/2009 | Goldstein et al. ............... | 381/74 |

* cited by examiner

*Primary Examiner* — Thjuan K Addy
(74) *Attorney, Agent, or Firm* — Marvin Petry; Stites & Harbison PLLC

(57) ABSTRACT

An ear device having a bubble for placement approximate a user's ear canal and capable of inflation and deflation. An inflation tube for delivering inflating air to the bubble during inflation of the bubble and an inflation source, such as a diaphonic valve, cause the bubble to extend automatically into the user's ear canal during inflation and retract from the user's ear canal during deflation. The bubble is substantially cylindrical and is comprised of a plurality of adjacently adjoined inflatable chambers. The bubble may also comprise at least one non-inflatable section interspersed therein. Where the ear device is used to convey sound to the user's ear, the device includes a sound tube positioned within the cylindrical bubble. At least one resilient member attached to a portion of the bubble, which may be a non-inflatable section of the bubble, is used to retract the bubble automatically. The ear device, equipped with a cerumen removing mechanism, may be used to clean a user's ear canal as well.

33 Claims, 7 Drawing Sheets

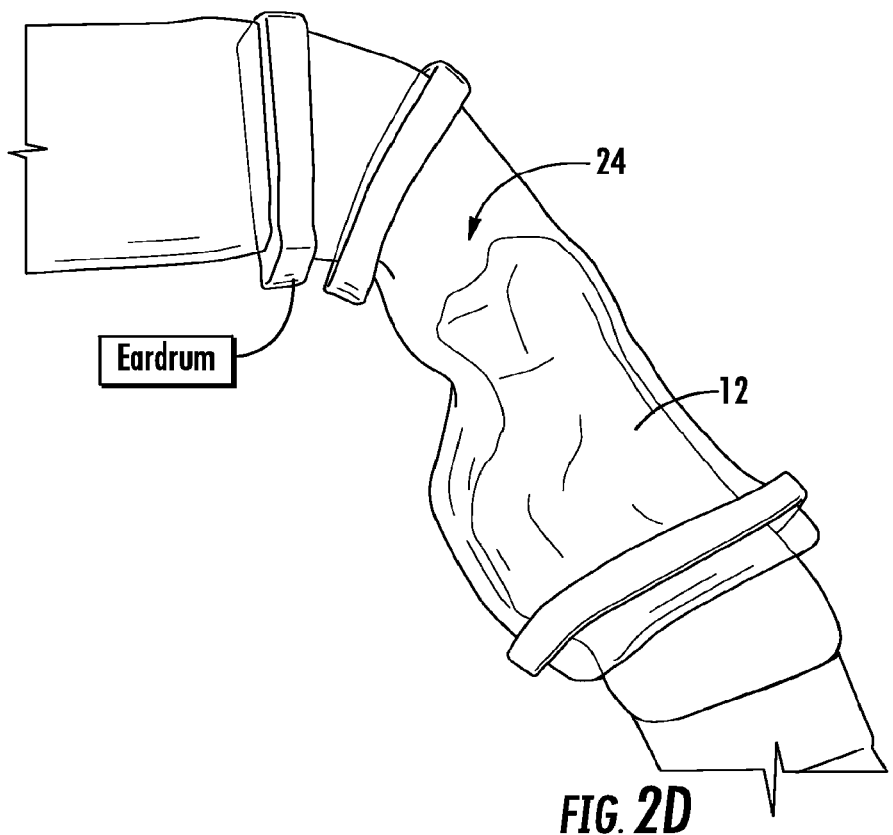
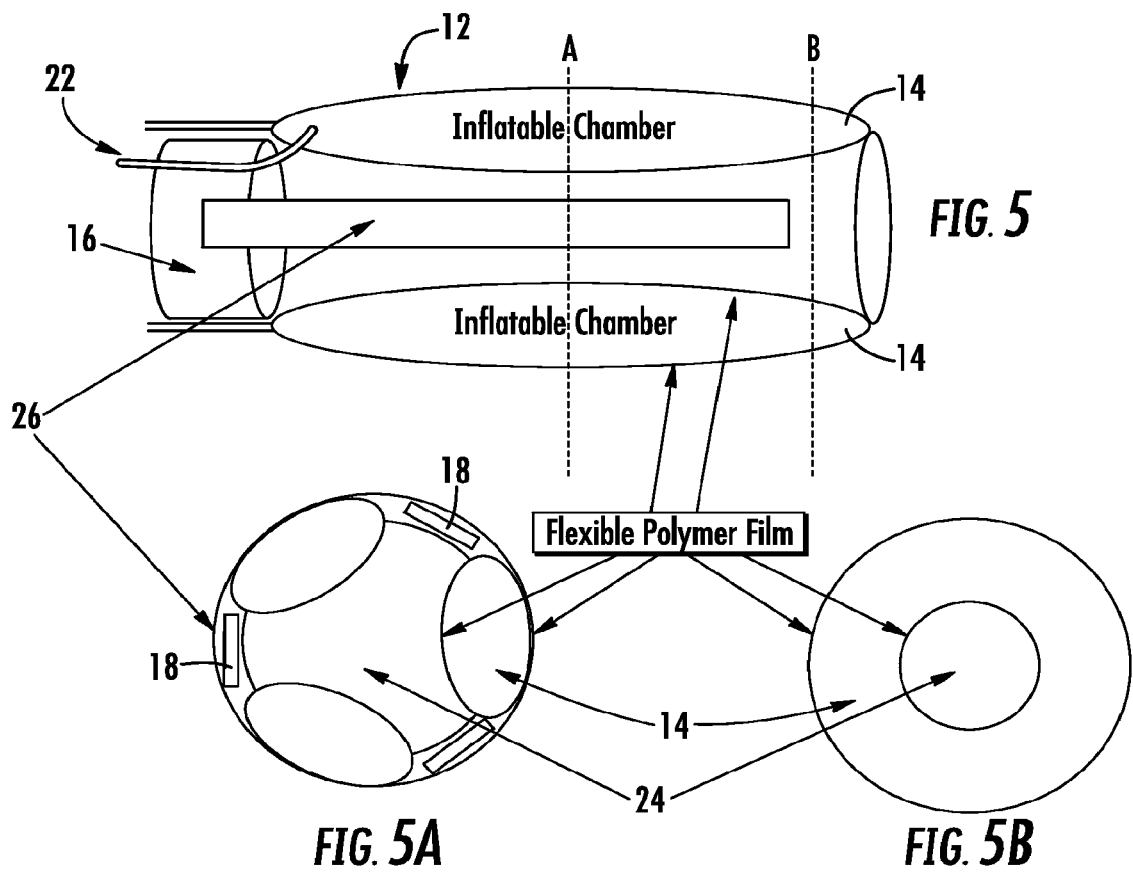

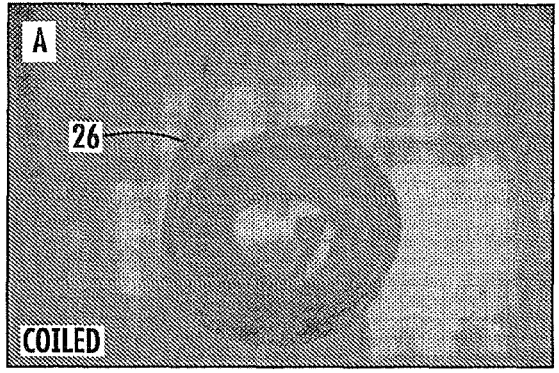
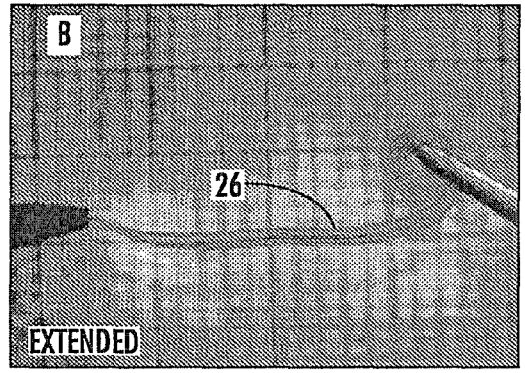
FIG. 6A  FIG. 6B
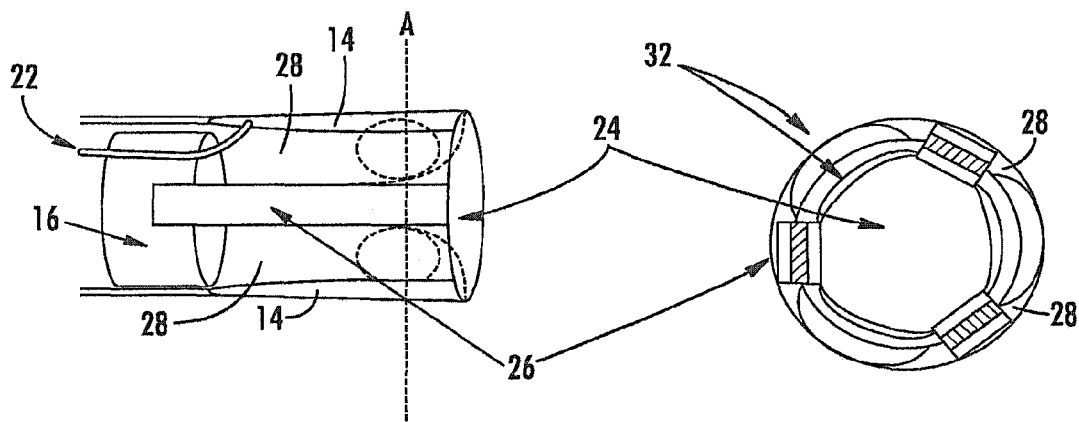
FIG. 7A
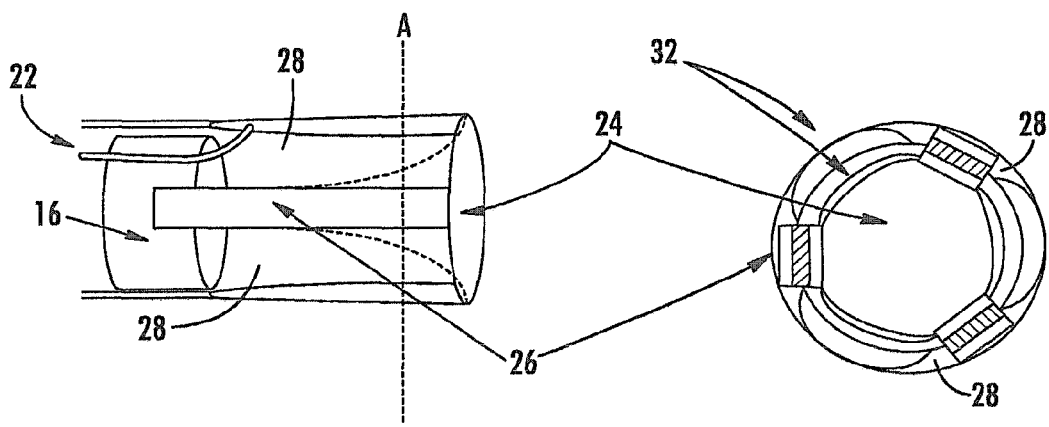
FIG. 7B

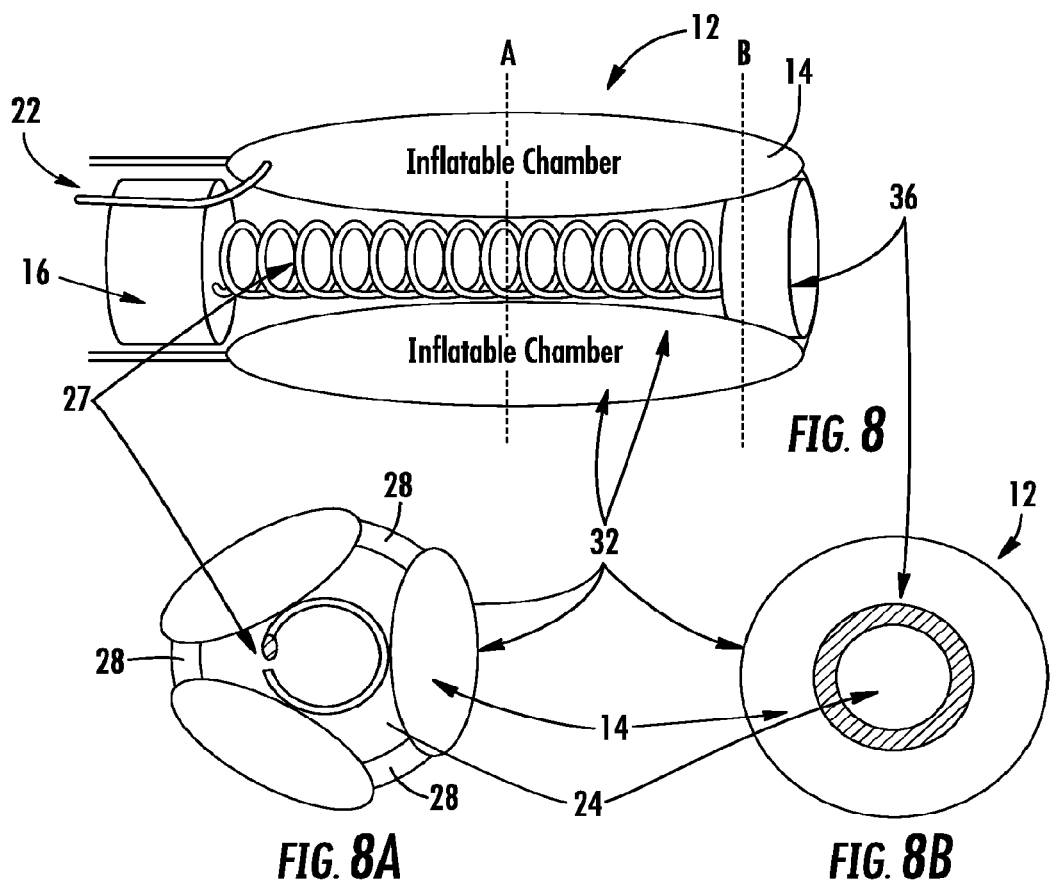
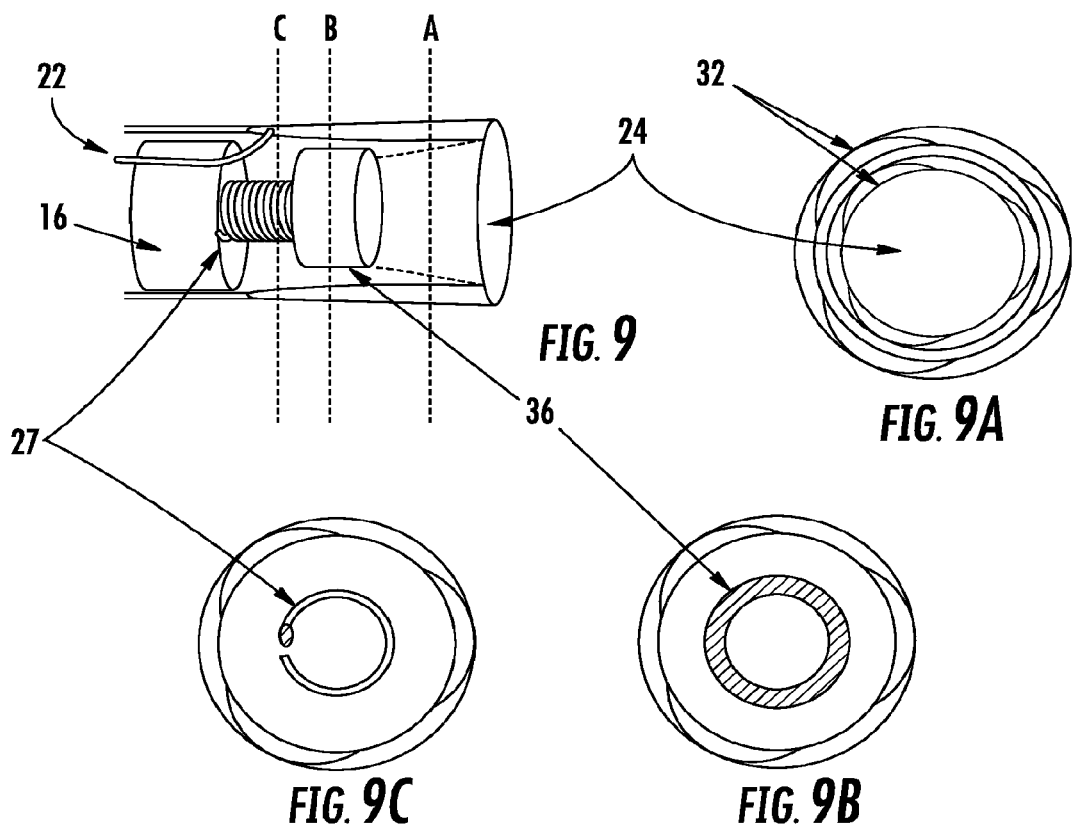

INFLATABLE BUBBLE

CROSS-REFERENCE TO RELATED APPLICATIONS

This application is a continuation of application Ser. No. 13/086,138, filed Apr. 13, 2011, which claims benefit of U.S. Provisional Application No. 61/323,599, dated Apr. 13, 2010. In addition, U.S. application Ser. No. 13/086,138, filed Apr. 13, 2011 is a continuation-in-part of U.S. application Ser. No. 12/777,001, to Ambrose et al., filed on May 10, 2010 and published as Publication No. 2010/0322454 A1 on Dec. 23, 2010, which is a continuation-in-part of U.S. application Ser. No. 12/178,236, to Ambrose et al., filed on Jul. 23, 2008 and published as Publication No. 2009/0028356 A1 on Jan. 29, 2009. The complete content of each of the above-listed applications is hereby incorporated by reference.

TECHNICAL FIELD OF THE INVENTION

The present device and methods relate to the structure, operation and manufacture of an insertable sound transmission instrument for a user's ear. Specifically, the device and methods relate to such an instrument which can be coupled with any number of electronic sound devices, such as a hearing aid, MP3 player, Bluetooth® device, phone, and the like, while providing improved comfort and control to the user.

BACKGROUND OF THE INVENTION

The use of headphones for private listening of an audio device, such as a phone, telegraph or the like, began back as early as the 1900's. The original devices provided very poor sound quality and even less comfort to the user. Such devices have come a long way in the last 20 years with noise-reduction, sound control, feedback control and comfort features as well. However, prior designs have typically employed a "one-size-fits-all" approach to function and comfort and as such they have been unable to offer an in-ear device which is individually customizable for a particular user. The present device addresses this oversight in the prior art by providing an in-ear device which is adjustable to comfortably fit each user, while providing full rich sound quality.

U.S. Patent Publication No. 2009/0028356 A1 (the '356 application), published on Jan. 29, 2009, discloses an in-ear, inflatable, diaphonic member (bubble), for the coupling of sound to the ear, wherein a source of static and active pressure is utilized to inflate the bubble and to keep it inflated. As part of the '356 application disclosure, a diaphonic valve is described that can convert oscillating sound pressure into static pressure to inflate the bubble in the user's ear. This is accomplished while still passing the sound of the program material (music, voice, etc.) through the valve, into the bubble and thus into the ear, with a minimum of attenuation or distortion. Thus a speaker or acoustical driver of the type used in hearing aids, mp3 player ear buds, or professional in ear monitors may be used to generate static pressures to inflate the diaphonic member (bubble), in addition to playing the program material. The diaphonic valve of the '356 application uses a flat valve design where oscillating sound waves cause oscillations in thin elastic membranes, thus opening and closing ports to harvest the positive pressure, pushing cycles of the speaker and venting in outside air during the negative pressure, pulling cycles of the speaker.

Embodiments of the present invention supplement the inventive pumping methods which utilize sound energy to actively inflate and deflate a diaphonic bubble in a user's ear by creating a bubble which expands in a completely unique manner.

The present invention addresses and solves numerous problems in the ear device industry and provides uncountable improvements in the area of earphone devices and manufacturing methods of the same. Solutions to other problems associated with prior earphone devices, whether the intended use is to be in conjunction with hearing aids, MP3 players, mobile phones, or other similar devices, may be achieved by the present devices.

SUMMARY OF THE INVENTION

There is disclosed herein an improved ear device for in-ear placement of a user which avoids the disadvantages of prior devices while affording additional structural and operating advantages.

Generally speaking, the invention of the present application, numerously embodied in countless combinations of components, is comprised of a bubble for placement approximate a user's ear canal and capable of inflation and deflation, and an inflation tube for delivering inflating air to the bubble during inflation of the bubble, wherein the bubble automatically extends into the user's ear canal during inflation and retracts from the user's ear canal during deflation. An inflating air source coupled to an end of the inflation tube is used to provide inflation air to the bubble. In a preferred embodiment, the inflating air source comprises a diaphonic valve.

In an embodiment of the invention, the bubble is substantially cylindrical and is comprised of a plurality of adjacently adjoined inflatable chambers. The bubble may also comprise at least one non-inflatable section interspersed therein. Where the ear device is used to convey sound to the user's ear, an embodiment of the invention includes a sound tube positioned within the cylindrical bubble.

An aspect of another embodiment comprises at least one resilient member attached to a portion of the bubble, which may be a non-inflatable section of the bubble. In one embodiment, the resilient member may comprise a coil spring positioned within the sound tube. In another, it may comprise at least one flat spring.

An ear device having a cerumen removing mechanism is also disclosed. The cerumen removing mechanism may be comprised of a textured outer surface on the bubble or a coating on an outer surface of the bubble. It is an aspect of an embodiment of the disclosed ear device to provide fibers selected from the group consisting of cotton fibers, linen fibers, polyester fibers, synthetic fibers, and any combination thereof within a bubble coating. Such fibers may be impregnated with a cleaning solution to soften or dissolve the cerumen.

Alternately, the ear device may be used exclusively as a cleaning device.

These and other aspects of the invention may be understood more readily from the following description and the appended drawings.

BRIEF DESCRIPTION OF THE DRAWINGS

For the purpose of facilitating an understanding of the subject matter sought to be protected, there are illustrated in the accompanying drawings embodiments thereof, from an inspection of which, when considered in connection with the following description, the subject matter sought to be protected, its construction and operation, and many of its advantages should be readily understood and appreciated. The components in the drawings are not necessarily to scale, emphasis instead being placed upon illustrating the principles of the invention. In the following description and throughout the numerous drawings, like reference numbers are used to designate corresponding parts.

FIGS. 2A through 2D illustrate the inflation and automatic insertion of the present ear device into an ear canal;

FIGS. 5, 5A, and 5B are side and cross-sectional illustrations of an embodiment of an inflatable bubble for the present ear device;

FIGS. 6A and 6B illustrate one embodiment of a resilient member, i.e., a flat spring, in a relaxed and a tensioned form;

FIG. 7A is a side view and cross-section of an inflatable bubble retracted using the mechanism of FIG. 3;

FIG. 7B is a side view and cross-section of an inflatable bubble retracted using the mechanism of FIG. 4;

FIGS. 8, 8A, and 8B are side and cross-sectional illustrations of another embodiment of an inflatable bubble for the present ear device; and FIGS. 9, 9A, 9B, and 9C are side and cross-sectional illustrations of the embodiment of FIG. 8 in a retracted state.

DETAILED DESCRIPTION OF PREFERRED EMBODIMENTS

Figure 1:
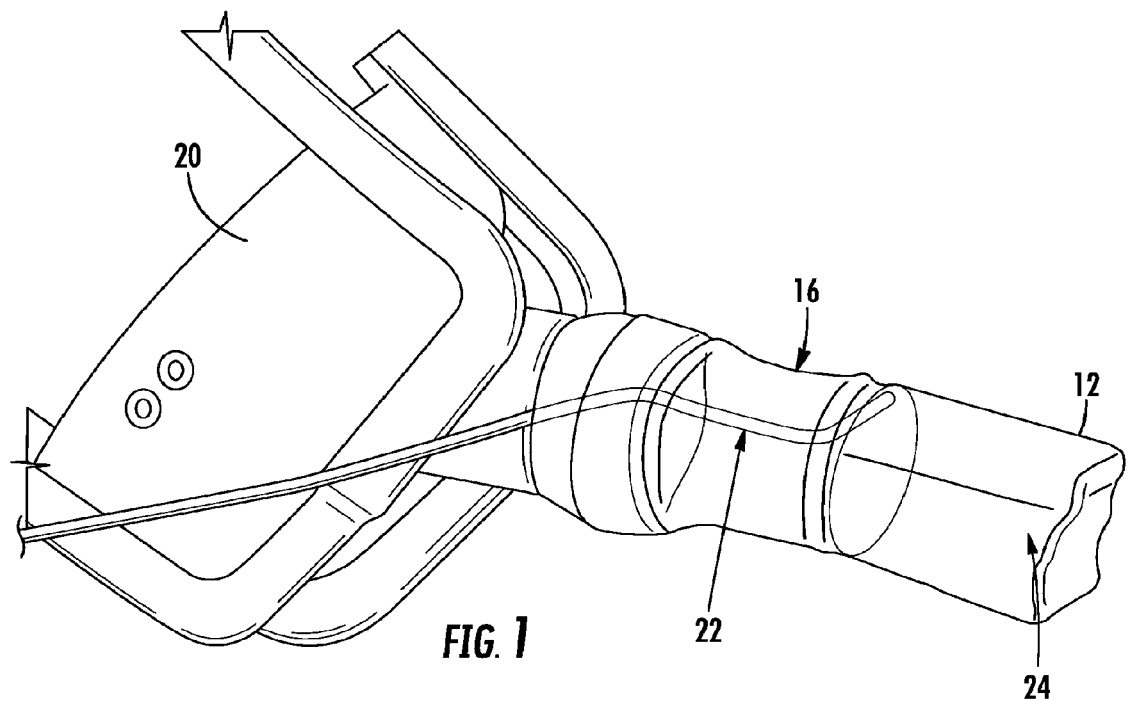
FIG. 1 is a perspective view of an embodiment of the ear device of the present application.

While this invention is susceptible of embodiment in many different forms, there is shown in the drawings, and will herein be described in detail, preferred embodiments of the invention, including embodiments of the various components of the invention, with the understanding that the present disclosure is to be considered as an exemplification of the principles of the invention and is not intended to limit the broad aspect of the invention to embodiments illustrated.

Referring to FIGS. 1-9, several embodiments of an automatic inserting ear device, generally referenced by the number 10. The ear device 10 is most generally comprised of a transducer 20, a bubble 12 comprised of multiple inflatable chambers 14, a coupling 16 for attaching the bubble 12 to the transducer 20, a resilient member 18 and an inflation tube 22 for delivering inflation air from the transducer 20 to the bubble interior.

The bubble 12 automatically operates between two forms: i.e., an inflated form and a deflated form. In the inflated form, the bubble 12 is unfurled and relatively firm, extending into a user's ear canal where it seals against the wall of the canal to retain the ear device 10 in place. When in the deflated form, the bubble 12 is refracted from the ear canal, flaccid and soft, and is pulled to some degree into or about itself. Specific details of the two forms and the operation of the bubble 12 to achieve such forms are explained in greater detail below.

Referring to FIG. 1, an embodiment of the automatic ear device 10 is illustrated with the bubble 12 in the deflated form and turned partially inside itself. The bubble 12 of the ear device 10 is shown attached to an ear piece 30 of an audio transducer 20. The inflation tube 22 is linked to a pressure output of a diaphonic valve (not shown) of the type described in previous patent and provisional application filings, each of which was incorporated herein to this application by reference above.

Figure 2A:
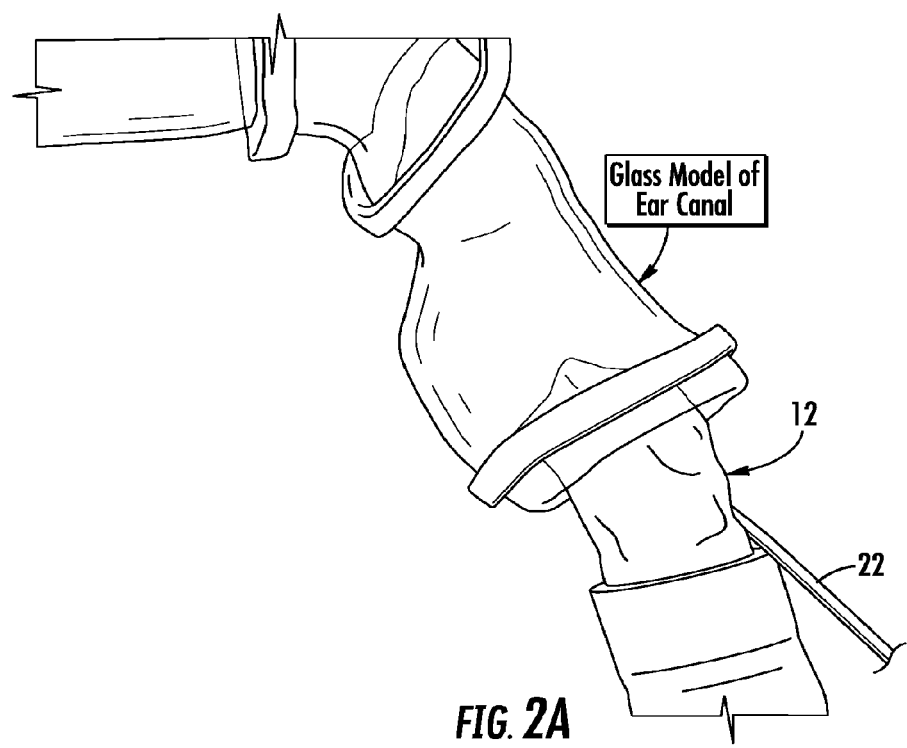
Figure 2B:
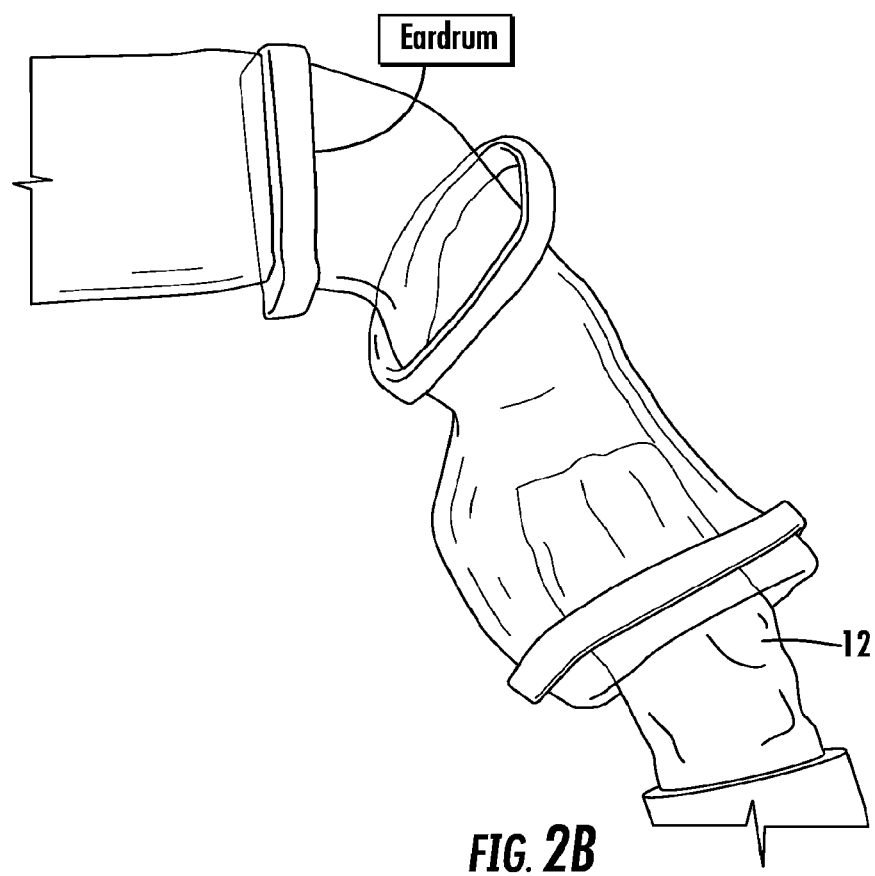
Figure 2C:
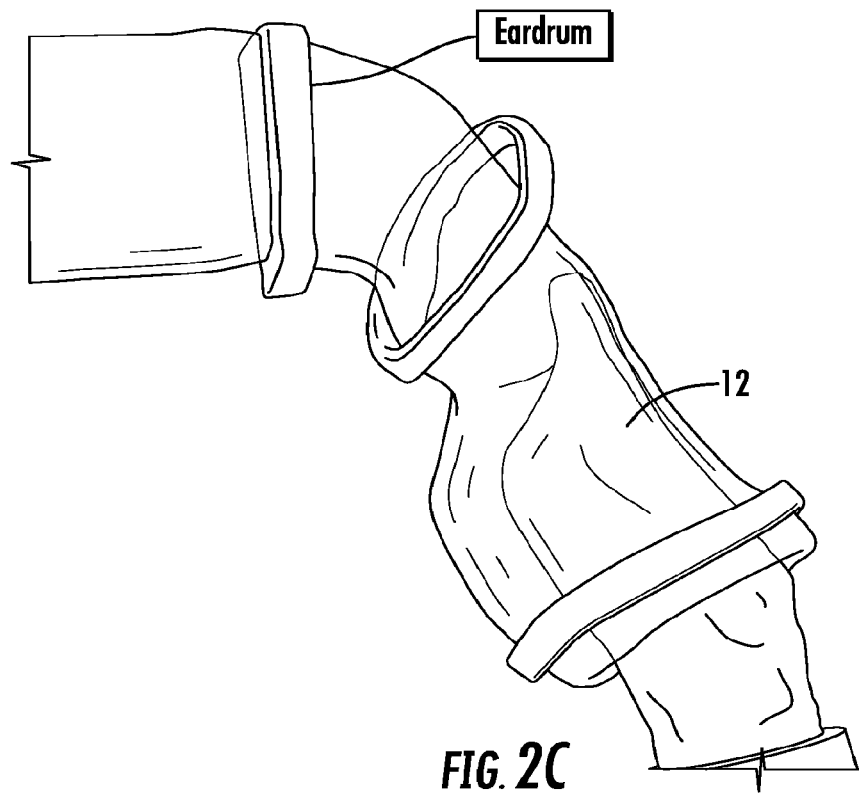

FIGS. 2A-2D are a series of drawings illustrating the inflation of the bubble 12 to automatically insert into a human ear canal. Beginning with FIG. 2A, the bubble 12 is shown positioned at the entrance to the ear canal before inflation begins. FIG. 2B shows the bubble 12 of the ear device 10 partially inflated and partially inserted into the ear canal as a result of the inflation. FIG. 2C shows the bubble 12 almost fully inflated and almost fully inserted into the ear canal. Finally, FIG. 2D shows the bubble 12 fully inflated and fully inserted into the ear canal, thus sealing against the walls of the ear canal to secure the device 10 as well as block out extraneous noise.

As can be seen, when fully inserted and fully inflated (FIG. 2D), the opening of the sound tube 24 at the end of the bubble 12 faces into the ear canal toward the tympanic membrane (ear drum). This is believed to be the most effective positioning in a majority of uses for the ear device 10.

Figure 3:
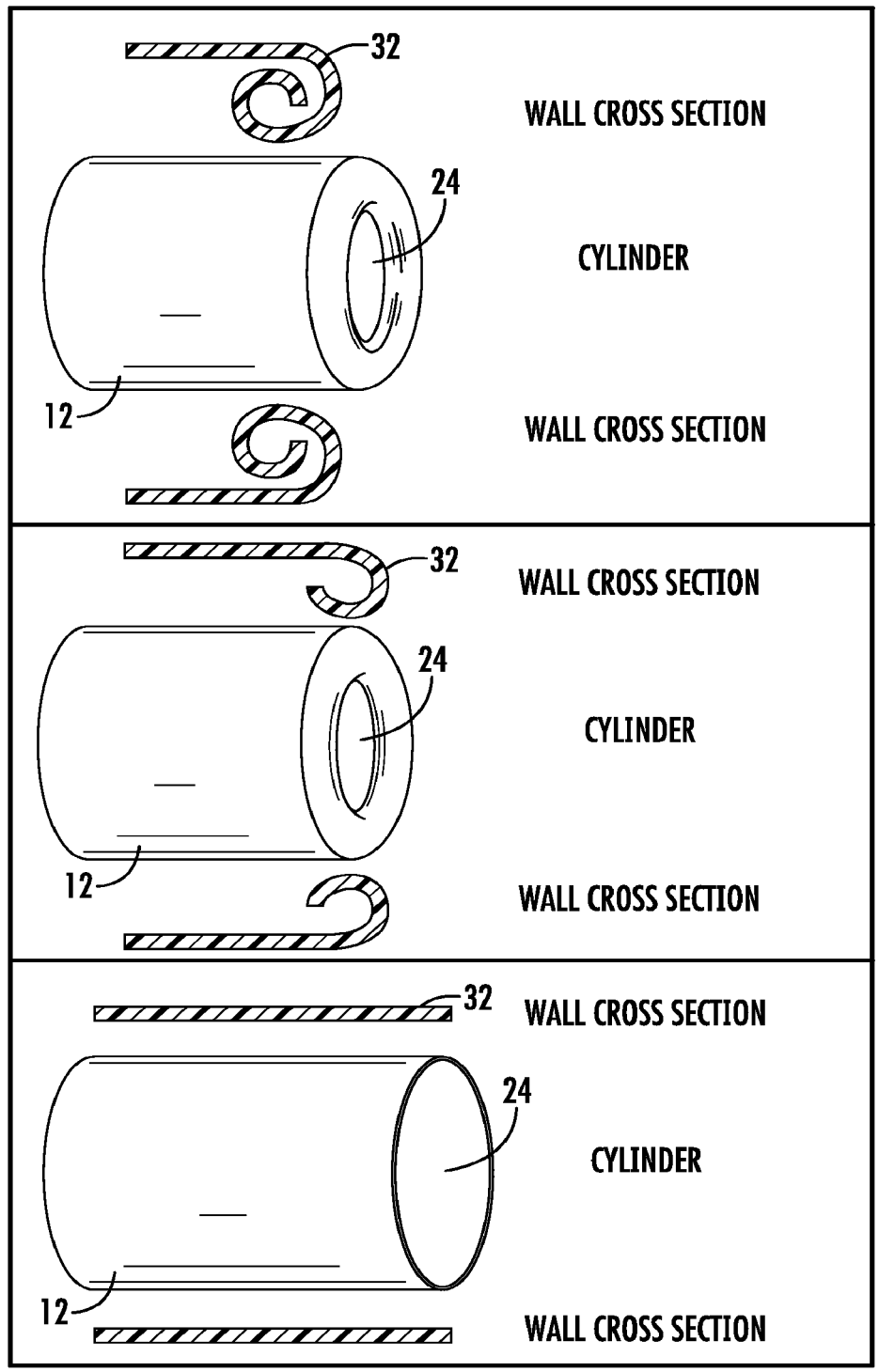
FIG. 3 diagrammatically illustrates one mechanism by which a cylindrical bubble may extend and contract in accordance with an embodiment of the present ear device.

Referring now to FIG. 3, a first mechanism by which the bubble 12 may be automatically inflated and inserted into the ear canal can be more readily understood. The first mechanism is probably best described as that of a cylinder rolled inward on itself from one of its ends. FIG. 3 illustrates in perspective and cross-section, the unrolling of such a cylinder.

Figure 4:
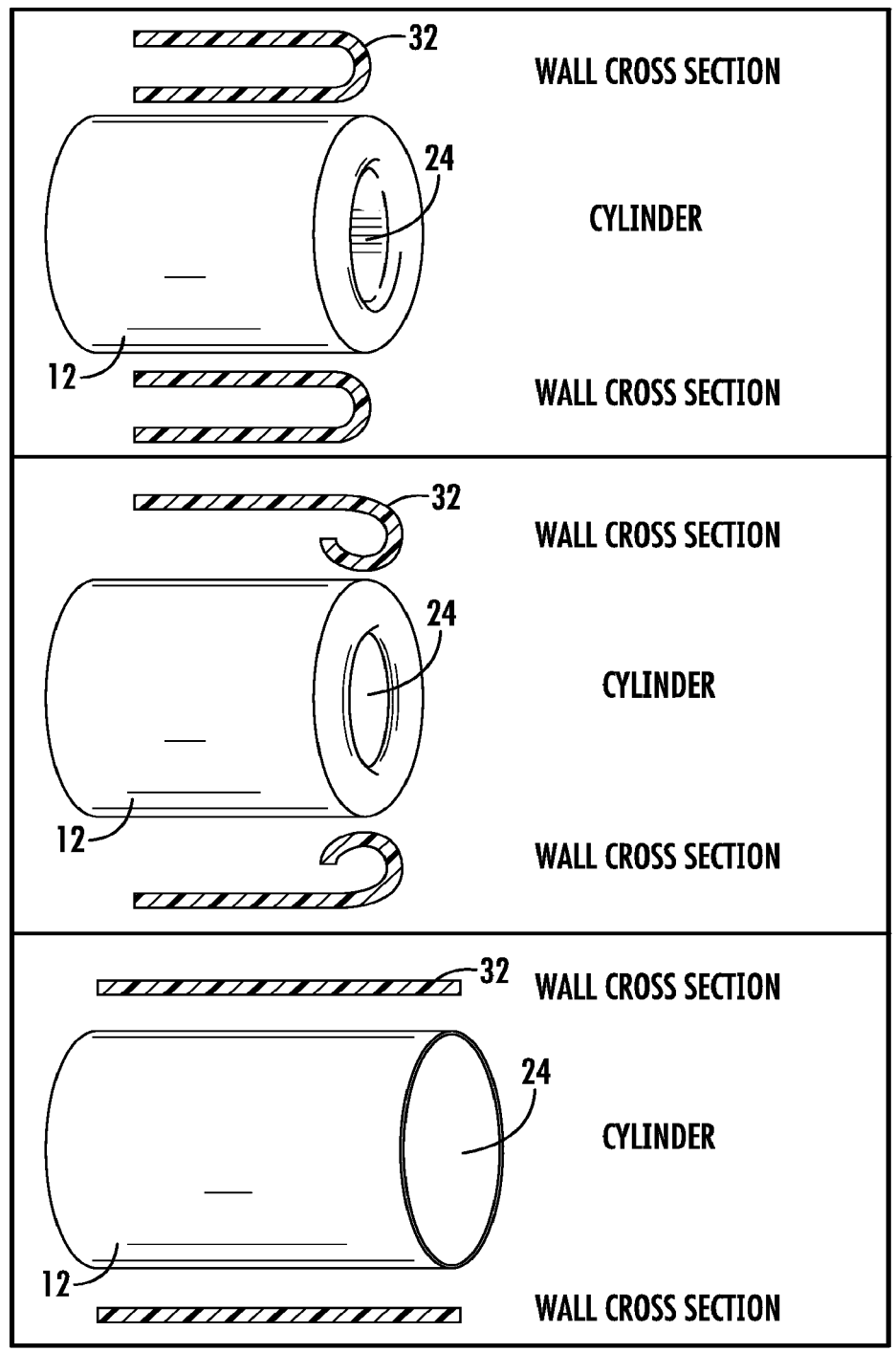
FIG. 4 diagrammatically illustrates another mechanism by which a cylindrical bubble may extend and contract in accordance with an embodiment of the present ear device.

FIG. 4 illustrates a second possible mechanism by which the bubble 12 of the ear device 10 may insert itself into the ear canal. In the second mechanism, the cylinder starts doubled over (or at least some fraction of its inflated form), the end folding inside the cylinder itself, as opposed to being rolled up inside itself as shown in FIG. 3. The mechanism of FIG. 3 is similar to that of rolling out a strip of rolled up carpeting (i.e. rolling out the red carpet). Contrastingly, the mechanism of FIG. 4 operates more like the motion of the treads of a tracked vehicle, such as a bulldozer or a tank (except that these mechanisms occur circumferentially because the layer is tubular). Both of these mechanisms are very effective at translating a layer (carpet or tank tread) forward along a surface. Various embodiments of the ear device 10 use one of the mechanisms of either FIG. 3 or FIG. 4 to "crawl up" the inside walls of the ear canal, without having to be slid, pushed or otherwise forced by the user into the ear canal.

The unrolling or unfurling of the bubble 12 from the ear device 10 is driven by the pumping of air into inflatable chambers 14 which make up the cylindrical bubble wall 32. This pumping is provided by a diaphonic valve of one of the numerous types previously disclosed. The re-rolling or re-furling of the bubble 12, i.e. the mechanism by which it retracts from the ear canal and turns inside itself, is driven by energy stored in a resilient member 18, such as a spring or springs. During inflation, air pressure pumped into the bubble 12 from the attached diaphonic pump unrolls or unfurls the rolled or furled portion of the bubble 12 and simultaneously places tension onto the resilient member, i.e., a flat spring or flat springs 26. As the air pressure is released in deflation mode, the spring or springs 26 begin to recoil, thereby re-rolling or re-furling the bubble 12.

FIGS. 5, 5A, and 5B show one particular embodiment of the mechanism by which the inflation and deflation is accomplished.

In the embodiment of FIG. 5 the cylindrical bubble wall 32 is composed of two layers of a flexible polymer film. This polymer film is preferably about one mil thickness of thermoplastic, elastomeric polyurethane (Bayer). However, the wall 32 could be comprised of any of the various elastomeric or flexible, but non-elastomeric polymer materials described in the incorporated references of this application. The bubble wall 32 may be divided lengthwise into sections, as opposed to being one single inflated chamber. The sections are preferably comprised of a plurality of inflatable chambers 14 interspersed with other non-inflatable sections. These inflatable chambers 14 preferably alternate with the non-inflatable sections 28. Further, the non-inflatable sections may contain constant force flat springs 26, shown fully extended in FIG. 5, to facilitate the furling or rolling of the bubble 12 during deflation.

FIGS. 6A-6B illustrate a flat spring 26, which is preferably made from polyvinylchloride (PVC). The flat spring 26 is shown in FIG. 6A in a fully coiled, relaxed state. In FIG. 6B the spring 26 is shown in a partially extended and thus partially tensioned state. Other embodiments have been constructed using steel flat springs and silicone rubber flat springs. A broad range of flat springs composed of a broad range of polymers, metals, or combinations of materials are appropriate for this application.

The particular embodiment of the ear device 10 shown in FIG. 5 has three flat springs 26 arranged every 120° around the circumference of the cylindrical bubble 12 and also three alternating similarly distributed inflatable chambers 14. In some embodiments, the wall sections containing the flat springs 26 may not extend all the way to the end of the bubble 12 and thus the inflatable chambers 14 may be connected to one another around the bubble circumference near the bubble end. Other embodiments may have a greater or lesser number of inflatable chambers 14 and flat springs 26 distributed around the bubble circumference. Further, the inflatable chambers 14 and flat springs 26 need not strictly alternate as shown in FIG. 5.

In alternate embodiments, some or all of the flat springs 26 may be housed in parallel inflatable chambers. The inflated, spring containing chambers may alternate or otherwise be arranged parallel to the non-spring containing inflated chambers. Still another alternative would be to have all the chambers around the bubble circumference be both inflatable and containing a flat spring.

As can be seen, the center of the bubble 12 is open and forms sound tube 24 by which sound is conducted from the transducer, into the user's ear canal, and directed toward the tympanic membrane.

FIGS. 7A-B illustrate the embodiment of FIG. 5 with the bubble 12 in an un-inflated, retracted state. The air has been discharged from the inflatable chambers 14 in the bubble wall 32 and the flat springs 26 have retracted causing the bubble wall 32 to roll into the sound tube 24 (FIG. 7A) or to fold into the sound tube 24 (FIG. 7B). Depending upon the detailed properties of the spring and bubble geometry, both folding mechanism (FIG. 7A or FIG. 7B) can be achieved.

FIGS. 8, 8A, and 8B illustrate another embodiment of a bubble 12 for the ear device 10. The bubble 12 is shown in its inflated and fully extended state, and uses a coil spring 27 rather than the flat springs of FIG. 7. In this embodiment there are only inflatable chambers 14 in the bubble wall 32—i.e., no chambers for springs—separated by seams where the inner and outer layers of the bubble wall 32 are joined. The inflation of the inflatable chambers 14 in the bubble wall 32 extends a coil spring 27 which is positioned in the middle of the sound tube 24. The coil spring 27 also acts to hold the sound tube 24 open during bubble use. Preferably, the spring 27 is connected by one end to a collar 34 used to hold the bubble 12 to the transducer 20 at the base of the bubble 12, and at its other end the coil spring 27 is attached to a sound tube collar 36 which is attached to the top of the bubble 12. The sound tube collar 36 is preferably made of thicker material (e.g., plastic, rubber, metal, etc.) than the thin walled bubble 12 and may be soft, semi-soft, rigid or semi-rigid. Alternatively, embodiments may be designed without the sound tube collar where the end of the coil spring 27 is affixed directly to the top of the bubble 12.

FIGS. 9, 9A-9C are similar to FIGS. 8, 8A, and 8B and illustrate retraction of the bubble 12 which occurs when air is let out of the inflatable chambers 14. As the air is removed, the coil spring 27 relaxes to its preferred, less elongated, state. The action of the coil spring 27 results in the bubble 12 folding into the sound tube 24 by the mechanism shown in FIG. 4.

While the use of a springs, either flat or coil as described above, are preferred as the resilient member, the same result may be achieved by the use of pressurized chambers which can be inflated and deflated to furl and unfurl a portion of the bubble 12.

An additional optional feature of the disclosed ear device 10 is that it may be used to clean ear wax (cerumen) from the user's ear. To accomplish this, the bubble 12 is constructed with an outer coating or texture which is readily adhered to by ear wax. Examples of such a texture would be, without limitation, ridges, bumps, grooves or even a fibrous surface texture. Examples of a suitable coating would include cotton fibers, linen fibers, polyester or other synthetic fibers, or a combination of these or other suitable materials. These fibers may also be impregnated with cleaning solutions for the purpose of softening/dissolving the cerumen.

In use, the ear device 10 with special surface coating or surface texture would be inflated into the user's ear canal. Once fully inflated, it may be necessary to give the special solutions time to work, then the device 10 can then be removed, either by deflating or by pulling directly out without deflating. Upon removal the surface of the device 10 pulls ear wax out of the ear. This cleaning system may be used with or without the audio listening component of the device.

It should be emphasized that the above-described embodiments of the present invention, particularly, any "preferred" embodiments, are possible examples of implementations merely set forth for a clear understanding of the principles for the invention. Many variations and modifications may be made to the above-described embodiment(s) of the invention without substantially departing from the spirit and principles of the invention. All such modifications are intended to be included herein within the scope of this disclosure and the present invention, and protected by the following claims.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

The invention claimed is:
1. An ear device comprising:
a base of a shape to be positioned proximate to a user's ear canal,
a longitudinally extendable bubble attached to the base and having an inflated state and a deflated state, the bubble having a distal end remote from the base,
wherein in moving from the inflated state to the deflated state, the distal end of the bubble is infolded longitudinally partially inside itself, and in moving to the inflated state, the distal end is unfolded longitudinally within the ear canal.

2. An ear device according to claim 1, including a diaphonic valve coupled to the bubble to provide air to inflate the bubble.

3. An ear device according to claim 1, including a resilient element attached to the bubble and biasing the bubble to the deflated state.

4. An ear device according to claim 3, wherein the resilient element is a flat spring which is biased to coil inwardly toward the base to roll the bubble inwardly during deflation.

5. An ear device according to claim 3, wherein the resilient element is a flat spring which is biased to roll over itself to fold the bubble inwardly during deflation.

6. An ear device according to claim 3, wherein the resilient element is a coil spring biased to its retracted position to bias the bubble inwardly during deflation.

7. An ear device according to claim 1, wherein the bubble comprises a plurality of longitudinally extending separate side by side inflatable chambers.

8. An ear device according to claim 7, wherein the inflatable chambers join each other, side by side.

9. An ear device according to claim 7, including a non-inflatable section located between adjacent inflatable chambers.

10. An ear device according to claim 1, including a sound tube extending from the base into the bubble.

11. An ear device according to claim 1, wherein the exterior of the bubble comprises a cerumen removing mechanism.

12. An ear device according to claim 11, wherein the cerumen removing mechanism comprises a coating on the outer surface of the bubble.

13. An ear device according to claim 12, wherein the coating comprises fibers selected from the group consisting of cotton fibers, linen fibers, polyester fibers, synthetic fibers and any combination thereof.

14. An ear device according to claim 13, wherein the fibers are impregnated with a cleaning solution.

15. An ear device according to claim 14, wherein the cleaning solution comprises a cerumen softening or dissolving solution.

16. An ear device according to claim 1, including an audio transducer coupled to the base.

17. An ear device comprising:
a base capable of being positioned proximate to a user's ear canal,
a bubble attached to the base and having an inflated state and a deflated state, and
including a resilient element connected to the bubble and exerting a bias thereon toward the deflated state.

18. An ear device according to claim 17, wherein the bubble is infolded longitudinally inside itself in moving to the deflated state.

19. An ear device according to claim 18, the resilient element being a flat spring which is attached to the bubble and biased so as to urge the bubble to its deflated state.

20. An ear device according to claim 18, wherein the resilient element is a coil spring.

21. An ear device according to claim 17, including a diaphonic valve which is connected to the bubble to inflate same.

22. An ear device comprising:
a base of a shape to be positioned proximate to a user's ear canal,
a bubble extending from the base and extendable into the user's ear canal,
the bubble having a longitudinally extending inflated state and a deflated state in which the bubble folds into itself, and
a diaphonic valve which delivers air into the bubble to inflate the bubble.

23. An ear device according to claim 22, including an inflation tube extending through the base and into the bubble, and the diaphonic valve being in communication with the inflation tube.

24. An ear device according to claim 23, including a transducer, and a sound tube extending from the transducer into the bubble.

25. An audio system comprising:
an ear device,
a base capable of being positioned proximate to the user's ear canal,
a bubble attached to the base and being capable of being inflated into the user's ear and retracted to a deflated state in which the bubble is folded into itself,
an inflation tube connected to an air source for inflating the bubble,
a resilient element connected to the bubble and connected to the base so as to exert a bias in the bubble toward the deflated position,
a sound source, and
a sound tube coupled to the sound source and transmitting sound into the bubble.

26. An audio system according to claim 25, including a diaphonic valve coupled to the bubble to provide air to inflate the bubble.

27. An ear device according to claim 25, wherein the sound source is a transducer.

28. An ear device according to claim 25, including a resilient element attached to the bubble and biasing the bubble to the deflated state.

29. An ear device according to claim 25, wherein the resilient element is a flat spring which is biased to coil inwardly toward the base to roll the bubble inwardly during deflation.

30. An ear device according to claim 25, wherein the resilient element is a flat spring which is biased to double over itself to fold bubble inwardly during deflation.

31. An ear device according to claim 25, wherein the resilient element is a coil spring which is biased to its retracted position to bias the bubble inwardly during deflation.

32. An ear device according to claim 1 wherein, in moving from the inflated state to the deflated state, the distal end of the bubble rolls up inside of the bubble.

33. An ear device according to claim 1, wherein in moving from the inflated state to the deflated state, the distal end is folded once and the distal end then moves longitudinally into the inside of the bubble.

* * * * *